US00PP12488P2

(12) United States Plant Patent
Trees

(10) Patent No.: US PP12,488 P2
(45) Date of Patent: Mar. 26, 2002

(54) GERANIUM PLANT NAMED 'BALCOLBUGI'

(75) Inventor: Scott C. Trees, Shell Beach, CA (US)

(73) Assignee: Ball FloraPlant, A Division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/822,012

(22) Filed: Mar. 31, 2001

(51) Int. Cl.[7] ..... A01H 5/00

(52) U.S. Cl. ..... Plt./332

(58) Field of Search ..... Plt./332

*Primary Examiner*—Bruce R. Campell
*Assistant Examiner*—Kent L. Bell
(74) *Attorney, Agent, or Firm*—C. A. Whealy

(57) ABSTRACT

A new and distinct cutlivar of Geranium plant named 'Balcolbugi', characterized by its burgandy-colored double flowers; cascading and mounded growth habit; freely basal branching habit; and medium green leaves with darker green zonation pattern.

1 Drawing Sheet

BACKGROUND OF THE INVENTION

The present invention relates to a new and distinct cultivar of Geranium plant, botanically known as *Pelargonium peltatum*, and hereinafter referred to by the name 'Balcolbugi'.

The new Geranium is a product of a planned breeding program conducted by the Inventor in Arroyo Grande, Calif. The objective of the breeding program was to develop new cultivars with freely-branching and vigorous growth habit, medium or dark green-colored foliage, uniform flowering, and interesting flower and foliage colors.

The new Geranium originated from a self-pollination made by the Inventor of the proprietary *Pelargonium peltatum* selection 8176-12. The cultivar 'Balcolbugi' was discovered and selected by the Inventor as a flowering plant within the progreny of the self-pollination in a controlled environment in Arroyo Grande, Calif., in 1998.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Balcolbugi'. These characteristics in combination distinguish 'Balcolbugi' as a new and distinct cultivar:

1. Cascading and mounded growth habit.

2. Freely basal branching habit.

3. Medium green leaves with darker green zonation pattern.

4. Burgundy-colored double flowers.

Plants of the new Geranium differ primarily from plants of the parent selection in flower form as flowers of the parent selection are semi-double and flowers of the new Geranium are double.

The new Geranium can be compared to the cultivar, 'Butterfly', not patented. However, in side-by-side comparisons conducted in Arroyo Grande, Calif., plants of the new Geranium differ from plants of the cultivar 'Butterfly' in the following characteristics:

1. Plants of the new Geranium are much more freely branching than plants of the cultivar 'Butterfly'.

2. Plants of the new Geranium have longer lateral branches but shorter internodes and more leaves per lateral branch than plants of the cultivar 'Butterfly'.

3. Plants of the new Geranium have smaller leaves than plants of the cultivar 'Butterfly'.

4. Plants of the new Geranium have smaller flowers than plants of the cultivar 'Butterfly'.

5. Plants of the new Geranium have fewer flowers per umbel than plants of the cultivar 'Butterfly'.

BRIEF DESCRIPTION OF THE PHOTOGRAPH

The accompanying colored photograph illustrates the overall appearance of the new cultivar, showing the colors as true as it is reasonably possible to obtain iin colored reproductions of this type. The photograph comprises a side perspective view of a typical flowering plant of 'Balcolbugi'. Flower and foliage colors in the photograph may differ slightly from the color values cited in the detailed botanical description which accurately describe the colors of the new Geranium.

DETAILED BOTANICAL DESCRIPTION

The cultivar 'Balcolbugi' has not been observed under all possible environmental conditions. The phenotype may vary somewhat with variations in environment such as temperature and light intensity, without, however, any variance in genotype. The following observations, measurements and comparisons describe plants grown 10-cm pots in Arroyo Grande, Calif., under commercial practice in a polycarbonate-covered greenhouse with day temperatures about 20 to 22° C., night temperatures about 18 to 20° C. and light levels about 2,500 to 3,000 foot-candles. Plants used for the photograph and description were about 8 to 10 weeks from planting rooted cuttings. In the following description, color references are made to The Royal Horticultural Society Colour Chart except where general terms of ordinary dictionary significance are used.

Botanical classification: *Pelargonium peltatum* cultivar 'Balcolbugi'.

Parentage:

*Female parent.*—Proprietary *Pelargonium peltatum* selection 8176-12.

*Male parent.*—Proprietary *Pelargonium peltatum* selection 8176-12.

Propagation:

*Type cutting.*—Terminal cuttings.

*Time to initiate roots.*—About 7 days at 18° C.

*Time to develop roots.*—About 21 days at 18° C.

*Root description.*—Fibrous, freely branching.

Plant description:

*General appearance.*—Cascading and mounded growth habit. Appropriate for 10-cm and larger containers.

*Crop time.*—Starting with a rooted cutting, about 8 to 10 weeks are required to produced a finished flowering plant in 10-cm container.

*Growth and branching habit.*—Vigorous and freely basal branching with about 9 lateral branches at the base. Pinching, that is, removal of terminal apices, is typically not required.

*Plant height* (*to top of foliage*).—About 13 cm.

*Plant width.*—About 35 cm.

*Lateral branches.*—Length: About 24 cm. Internode length: About 2.1 cm. Color: Between 146B and 147B.

*Foliage description.*—Leaves simple, generally symmetrical, abundant, opposite. Quantity of leaves per lateral branch: About 14. Length: About 3.7 cm. Width: About 6.4 cm. Shape: Reniform. Apex: Acute. Base: Cordate. Margin: Palmatifid; entire. Venation: Palmate. Texture: Smooth; slightly pubescent along veins of lower surface. Color: Young foliage, upper surface: 137A; zonation pattern, close to 139A in color and located at center of leaf. Young foliage, lower surface: 137C. Fully expanded foliage, upper surface: Darker than 137A; zonation pattern, close to 139A color, about one-third of the leaf width and located at center of leaf. Fully expanded foliage, lower surface: Closest to 137C. Venation, upper and lower surfaces: 146C. Petiole: Length: About 6.5 cm. Diameter: About 2 mm. Color: Between 146B and 147B.

Flower description:

*Flower arrangement and type.*—Burgundy-colored flowers arranged in hemispherical umbels arising from apical leaf axils. Umbels displayed above the foliage. At full flowering, usually about 6 open umbels and about 2 developing umbels per plant. Flowers double and rounded in shape. Umbels persistent. Flowers not fragrant.

*Flowering season.*—Year-round under greenhouse conditions. In the garden, flowering is continuous from spring until fall.

*Umbels.*—Number of flowers per umbel: About 6. Diameter: About 7.7 cm. Height: About 4.5 cm. Flower diameter: About 5 cm.

*Flower buds.*—Length: About 1.8 cm. Diameter: About 9 mm. Shape: Ovoid. Color: Before showing color, 138A; when showing color, mottled, 155D and between 53A and 59B.

*Petals/petaloids.*—Quantity: About 10 petals and about 3 to 9 petaloids per flower. Petaloids viariable in size and shape. Arrangement: Imbricate. Petal length: Upper petals: About 2.8 cm. Lower petals: About 2.5 cm. Petal width, upper and lower petals: About 1.8 cm. Petal shape: Obovate. Petal/petaloid apex: Rounded. Petal/petaloid base: Attenuate. Petal/petaloid margin: Entire. Petal/petaloid texture: Velvety Petal/petaloid color: Upper surface: Between 53A and 59A; venation towards base, 59A. Lower surface: Mottled, 155D and 61B; margin, 61B.

*Sepals.*—Quantity: About 5, not imbricate. Length: About 1.4 cm. Width: About 3 mm. Shape: Ensiform. Apex: Narrowly acute. Margin: Entire. Texture: Pubescent. Color, upper and lower surfaces: 138A.

*Peduncle* (*umbel stem*).—Length: About 14.6 cm. Angle: Erect. Strength: Strong. Texture: Sparsely pubescent. Color: Between 146A and 147B.

*Pedicel* (*individual flower stem*).—Length: About 2.6 cm. Angle: Erect. Strength: Strong. Texture: Slightly pubescent. Color: 146C; slight reddish purple anthocyanin towards flower.

*Reproductive organs.*—Androecium: Anther quantity: About 11. Anther length: About 2.2 mm. Anther color: Closest to 82B. Pollen amount: Moderate. Pollen color: Closest to 168B. Gynoecium: Pistil quantity: One. Pistil length: About 1.5 cm. Stigma shape: Five-parted, star-shaped. Stigma color: Closes to 53A. Style length: About 3 mm. Style color: Closest to 155D.

*Seed.*—Not observed.

Disease resistance: Resistance to pathogens common to Pelargonium has not been observed.

It is claimed:

1. A new and distinct cultivar of Geranium plant named 'Balcolbugi', as herein illustrated and described.

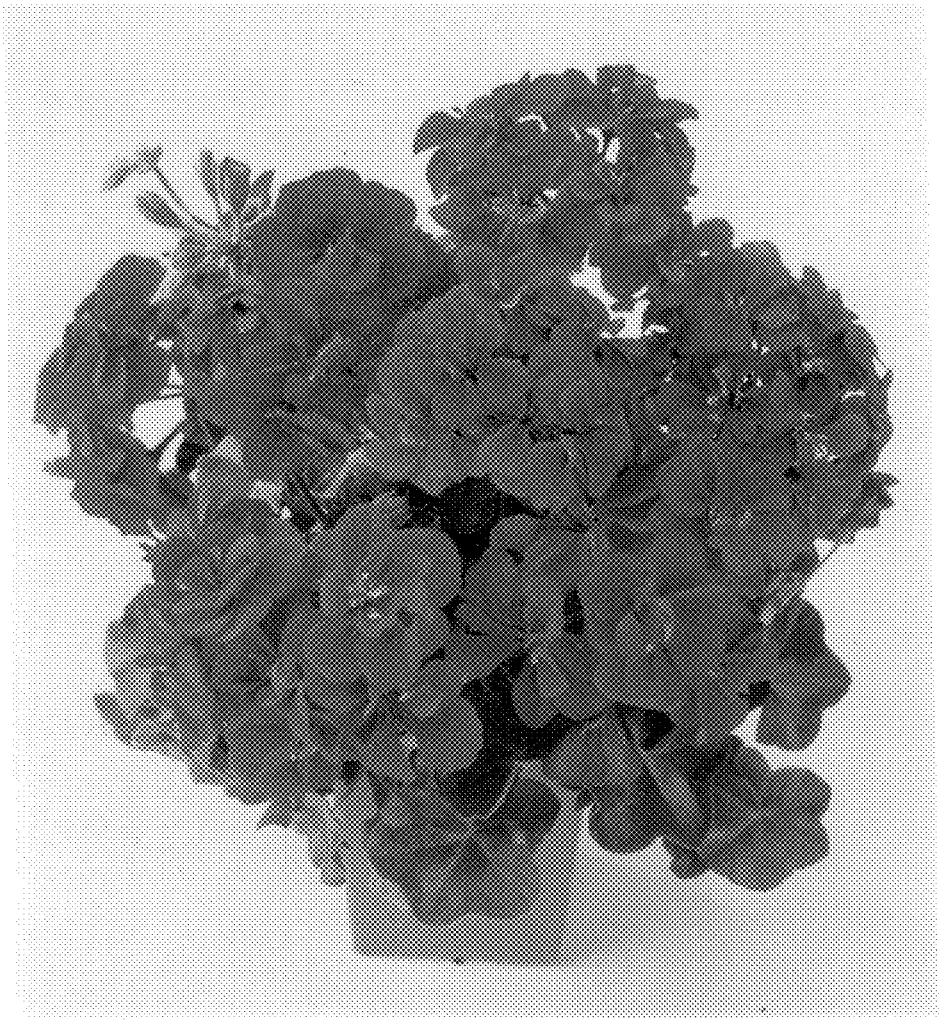

* * * * *